United States Patent [19]

Cole et al.

[11] Patent Number: 5,365,067
[45] Date of Patent: Nov. 15, 1994

[54] METHOD AND DEVICE FOR EVALUATION OF SURFACE PROPERTIES, ESPECIALLY MOLECULAR ORIENTATION, IN NON-TRANSPARENT LAYERS

[75] Inventors: Kenneth Cole, St. Hubert; Paolo Cielo, Montréal; Michel M. Dumoulin, Mont. St. Hilaire; Jacques Guévremont, Montréal, all of Canada

[73] Assignee: National Research Council of Canada, Ottawa, Canada

[21] Appl. No.: 83,468

[22] Filed: Jun. 30, 1993

[51] Int. Cl.$^5$ ............................................. G61J 4/00
[52] U.S. Cl. .............................. 250/341.8; 250/339.07; 356/369
[58] Field of Search ................ 250/341, 339; 356/369, 356/364, 367

[56] References Cited

U.S. PATENT DOCUMENTS

| | | | |
|---|---|---|---|
| 4,015,127 | 3/1977 | Sharkins | 250/341 |
| 4,264,207 | 4/1981 | Batyrev et al. | 356/364 |
| 4,631,408 | 12/1986 | Zelmanovic et al. | 250/341 |
| 4,908,508 | 3/1990 | Dubbeldam | 356/369 |
| 4,909,630 | 3/1990 | Gawrisch et al. | 356/364 |
| 5,157,259 | 10/1992 | Suettinger et al. | 356/364 |
| 5,181,080 | 1/1993 | Fanton et al. | 356/369 |

Primary Examiner—Paul M. Dzierzynski
Assistant Examiner—Drew A. Dunn
Attorney, Agent, or Firm—Juliusz Szereszewski

[57] ABSTRACT

A method and apparatus for determining surface molecular orientation and related properties of an opaque polymeric sheet relies on the detection of relative intensity of spectral reflectance in at least one polarized beam reflected from the surface of the sheet rather than transmitted therethrough. The relative intensity is affected by the preferential orientation of the polymeric chains. The method is fast and can be applied on-line at a speed of the running sheet as high as 1000 m/s.

5 Claims, 4 Drawing Sheets

METHOD AND DEVICE FOR EVALUATION OF SURFACE PROPERTIES, ESPECIALLY MOLECULAR ORIENTATION, IN NON-TRANSPARENT LAYERS

FIELD OF THE INVENTION

This invention relates to the evaluation of surface molecular orientation and related properties, such as crystallinity, in thick or non-transparent layers of material, and especially to on-line evaluation of surface molecular orientation in thick polymeric sheets or layers.

BACKGROUND OF THE INVENTION

In a typical hot rolling process for a polymeric sheet, the polymer being e.g. polyethylene-terephthalate (PET) or polyethylene (PE), the extrudate is subjected to successive rolling operations reducing its thickness. The resulting polymeric sheet and the rollers are typically maintained at temperatures below but near the melting point of the polymer during the process.

Due to rolling, directional elongation and also, sometimes, to additional stretching, the polymer sheet acquires an orientation, i.e. the molecular chains become preferentially oriented in the longitudinal direction (parallel to the sheet movement). On-line evaluation of such orientation would be useful for both quality and process control since the orientation directly affects the mechanical properties of the polymer sheet. Ideally, such methods should be non-contact so as to introduce no perturbation to the ongoing process.

Prior art methods and techniques for evaluating molecular orientation involve ultrasonic velocity anisotropy, thermal anisotropy, X-ray diffraction, optical birefringence and optical dichroism measurements. Another technique requiring a transmission configuration is small-angle light scattering, as described in U.S. Pat. No. 4,264,207 by Batyrev et al. This technique is, however, affected both by molecular and microstructural orientation, while also being very sensitive to directional surface roughness.

Ultrasonic velocity anisotropy requires transmitting of ultrasonic radiation in different directions within the polymer. This typically requires liquid contact of the transducer with the material.

Thermal anisotropy can be monitored without contact by heating a spot on the sheet surface by a focused laser beam and monitoring the ellipticity of the temperature distribution around the heated spot by a thermographic camera. However, the thermal response is slow due to the low thermal diffusivity of the polymer, while induced localized temperature gradients may interfere with the viscoelastic rolling process.

X-ray diffraction is often used to evaluate crystalline and oriented materials, but this technique is not appropriate to on-line applications because it is expensive, unsafe and very sensitive to positioning.

Optical birefringence, i.e. a difference in the refractive index values depending on the polarization of the incident light beam, is strongly related to molecular orientation. Birefringence can be measured for example with a set-up as shown in FIG. 1: a light beam polarized either parallel or perpendicular to the plane of the figure is totally reflected at the interface between a prism 11 and a polymer film 10 in good contact with the prism, up to a critical value of the angle of incidence at which some light starts leaking into the film 10. As the critical angle depends on the film's refractive index, and this index is different for the two polarizations of the light beam, one can evaluate the two refractive indices, and thus the birefringence, by measuring the critical angles corresponding to the two polarizations of the incident light beam. This technique requires a good contact, usually via a matching liquid, and therefore is inadequate for on-line applications.

Non-contact birefringence techniques are also possible, e.g. by monitoring the phase retardation induced by the insertion at different angles of a polymer film in a polarized interferometer, as described in U.S. Pat. Nos. 4,909,630 to Gawrisch et al. and 4,973,163 to Sakai et al, but this typically requires a clear and smooth, usually very thin, polymer film.

Similar to birefringence is the measurement of optical dichroism i.e. a difference in the material absorbance depending on the polarization of the light beam transmitted through the polymer film 12 as shown in FIG. 2. The atoms which make up a polymer molecule vibrate according to well defined normal modes, many of which are highly localized on particular chemical bonds or groups of bonds. Certain vibrational modes produce a fluctuation in dipole moment known as the transition moment, which has a specific direction with respect to the long chain of the polymer molecule. The absorption of electromagnetic radiation is determined by the angle between the transition moment and the electric field vector of the radiation. The absorption intensity of a particular mode is the greatest when the two are parallel and zero when they are perpendicular. This is the basis of optical dichroism. A preferential orientation of the polymer chains results in a preferential orientation of the transition moments and hence a preferential absorption of light polarized with its electric vector parallel to the transition moments.

The measurement is typically performed by spectropolarimetry: light of different polarizations transmitted through a film 12 is spectrally analyzed by a monochromator (see, e.g. U.S. Pat. No. 4,309,110 by Tumerman) or a spectrometer (not shown in FIG. 2); if the film has transition moments preferentially aligned, say, in the plane of the figure, light polarized parallel to the plane of the figure will be preferentially absorbed. The corresponding spectral absorption band will thus be very strong with this polarization, while being much weaker when the incident light beam is polarized perpendicular to the plane of the figure. Again, this typically requires a clear and usually very thin polymer film (whose thickness must be of the order of the light penetration depth on the spectral absorption band—typically 1 to 50 micrometers), which is not the case for the typically 1 mm thick sheet in question.

SUMMARY OF THE INVENTION

It is an object of the present invention to provide a fast, simple, non-contact method and device for on-line analysis of surface molecular orientation and/or related properties such as crystallinity, of a polymeric sheet of a material even if the sheet is very thick or optically opaque.

According to the invention, there is provided a method of determining the surface molecular orientation and related properties such as crystallinity, of a polymeric sheet, comprising:

directing a substantially collimated optical radiation beam onto the surface of the sheet to produce a reflected optical radiation beam, extracting at least one plane-polarized component of the reflected optical radiation beam, detecting the intensity of the at least one component within at least one selected spectral band, and, analyzing the intensity of said at least one component of the reflected optical radiation beam by comparison with a reference intensity.

In an embodiment of the invention, the method comprises:

directing a substantially collimated optical radiation beam onto the surface of a polymeric sheet to produce a reflected optical radiation beam, splitting the beam into two components having different orthogonal polarization, detecting the intensity of each of the two components within at least one selected spectral band, and analyzing said intensity of each component by comparison with a reference intensity.

In another aspect of the invention, there is provided an apparatus for determining spectroscopically significant surface properties, such as surface molecular orientation, of a polymeric sheet, the apparatus comprising:

means for directing a radiation beam at the surface of the polymeric sheet so as to produce a radiation beam reflected from the surface, means for extracting at least one plane-polarized component of the reflected radiation beam, and means for detecting the intensity of the at least one plane-polarized component of the reflected radiation beam.

Preferably, the apparatus comprises means for extracting two polarized components of the reflected radiation beam and means for detecting their respective intensity. Further, the apparatus may comprise means for detecting and analyzing the intensity in at least one selected spectral band. The intensity of the polarized component or components is analyzed by comparison with a reference intensity, characteristic to a non-oriented material, which may be the intensity of one of the two components.

The radiation may include IR spectrum, UV spectrum or visible light. The presence of the visible spectrum is advantageous for the positioning of the beam. Preferably, the infrared spectrum is included as it offers better selectivity than visible or UV light in the identification of molecular orientation.

The incident radiation beam may be directed normally at the sheet surface. Alternatively, the incident beam can be directed onto the surface at a predetermined angle.

BRIEF DESCRIPTION OF THE DRAWINGS

Exemplary embodiments of the invention will be described in conjunction with the drawings, in which.

DESCRIPTION OF PREFERRED
EMBODIMENTS OF THE INVENTION

It is known in the art of polymer processing that the quality of the surface of an extruded polymeric sheet may vary depending on the processing conditions. In certain cases, rough or embossed surface is obtained deliberately; in others, this is a result of a processing fault. It is important to realize that the present invention relies on a high degree of relatively collimated reflection of the incident radiation beam. A surface of significant roughness would produce considerable scattering of the reflected beam which would in turn contribute to a higher error margin of the present approach. For the purpose of the present invention, the surface roughness amplitude should ideally be much smaller than the projected wavelength, typically about 10 micrometers.

Figure 1:
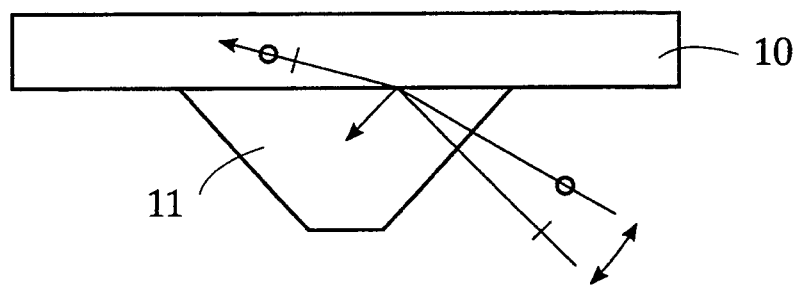
FIG. 1 is a schematic illustration of prior art birefringence measurement by polarized total reflection.

Referring now to the drawings, FIG. 1 illustrates prior art birefringence measurement by polarized total reflection, as discussed in the background of the invention. The figure illustrates the importance of the critical value of the angle of incidence. A polymeric film 10, at least partially transparent, is in contact with a prism 11. It can be seen that the critical angle, at which some light starts leaking into the film, has been reached.

Figure 2:
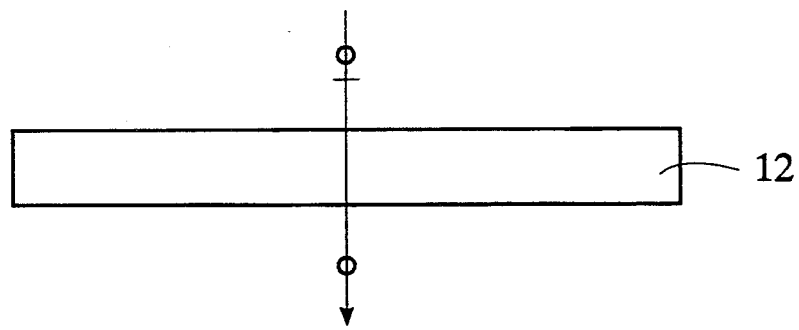
FIG. 2 is a schematic illustration of prior art dichroism measurement by polarized spectral transmittance.

FIG. 2, as explained above, illustrates the prior art measurement of optical dichroism. A light beam is transmitted through a polymer film 12 and a difference in the material absorbance dependent on the polarization of the light beam is determined.

Figure 3:
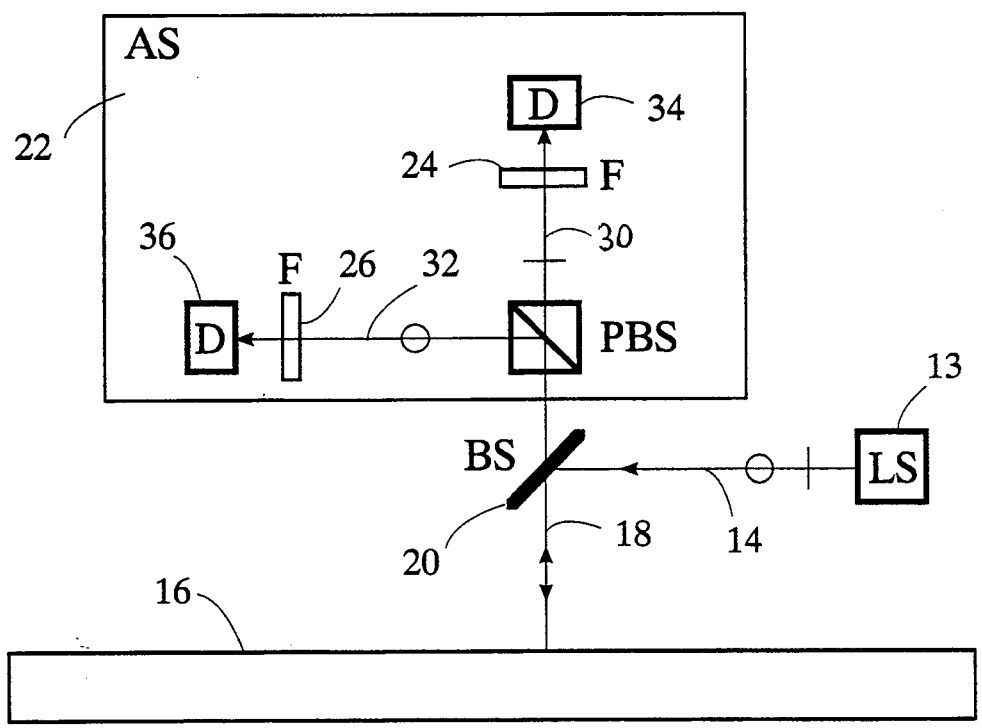
FIG. 3 is a schematic illustration of an embodiment of the device of the present invention.

In an embodiment of the present invention illustrated in FIG. 3, a non-polarized, wide-band infrared light source (LS) 13, such as a Globar or other heated-filament radiation source, projects a nearly collimated light beam 14 normally onto the surface of a polymeric plate 16 to be analyzed. The reflected light beam 18 is transmitted through a beam splitter (BS) 20 to an analyzing system (AS) 22 which provides a spectral-polarization analysis of the reflected light beam containing the information on the surface molecular orientation or the other properties of the surface as mentioned hereinabove. The analyzing system includes a polarizing beam splitter PBS which splits the light reflected by the plate into two beams 30, 32, polarized parallel and perpendicular, respectively, to the plane of the figure; bandpass optical filters, or spectral filters (F) 24, 26 which select an absorption band corresponding to a directional transition moment; and two filtered detectors 34, 36.

The basic difference between optical dichroism measurement (FIG. 2) and the present invention is that the latter proposes to measure surface dichroism by monitoring the intensity of the reflection at the air-polymer interface. Indeed, if the directional polymer molecules have a strong absorption at a given wavelength for light polarized parallel to the direction of the molecule, the surface reflectivity will be very high for this polarization according to the formula $$R = \left( \frac{n + ik - 1}{n + ik + 1} \right)^2$$

where
- n is the real part of the refractive index,
- k is imaginary part of the refractive index (related to absorption) and
- i is the imaginary unit while being lower for the orthogonal polarization. Consequently, the two detectors will sense different signals if the molecules at the plate surface are oriented in a given direction, while giving the same signal if the molecules are isotropically distributed at the plate surface. This is convenient for thick or opaque sheets or plates; for thin clear sheets a well-known transmission configuration of the kind shown in FIG. 2 may be used to sense the average molecular orientation through the sheet thickness.

Figure 4:
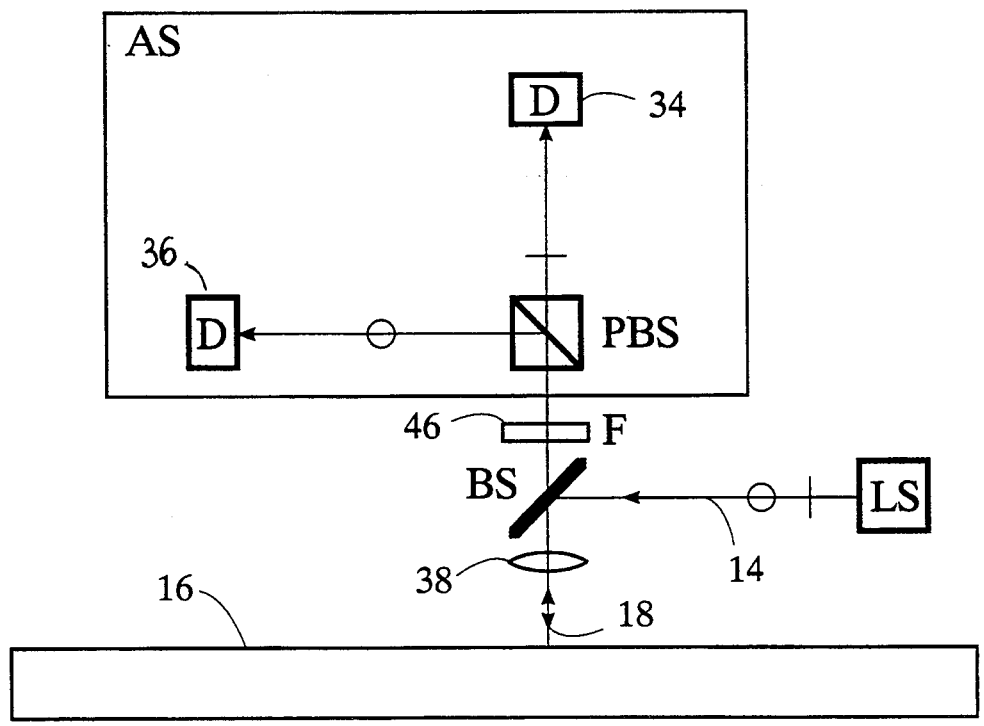
FIG. 4 is a schematic illustration of another embodiment of the device of the invention.

Another embodiment of the device of the invention, shown in FIG. 4, differs from the one of FIG. 3 by the provision of a lens (L) 38 which facilitates the focusing of the incident beam 14 and the reflected beam 18, and the replacement of two spectral filters 24 and 26 by one filter 46 positioned between the polarizing beam splitter (PBS) and the beam splitter (BS).

Alternatively, one could filter and polarize the light beam prior to projection or use a laser source of appropriate infrared wavelength whose direction of linear polarization may be rapidly rotated by known techniques. However, the configuration shown in FIG. 3 has the advantage of projecting both infrared and visible light from the wide-band source onto the plate surface, which facilitates the visual adjustment and positioning of the light beam. One might also use a third polarizer to extract a third independent polarization component, or else rotate the full system around the normal to the surface if a full scan of the reflected light polarization is required. This allows the determination of the direction in which the orientation is maximized.

Each filtered detector 34, 36 of FIG. 3 may be replaced (FIG. 5) by a pair of detectors 38, 40, and 42, 44 filtered by means of filters $F_1$ and $F_2$ over two different spectral bands $\lambda_1$ and $\lambda_2$ respectively, corresponding to orthogonal transition moments if a ratio measurement is preferred, or by arrays of detectors following a dispersive element such as a diffraction grating or a prism, as is known in spectrometer technology. Observation of several wavelengths may be useful, e.g. to simultaneously monitor absorption bands related to material properties other than orientation such as crystallinity peaks, or to evaluate orientation at widely different wavelengths having different penetration depths below the surface.

Figure 5:
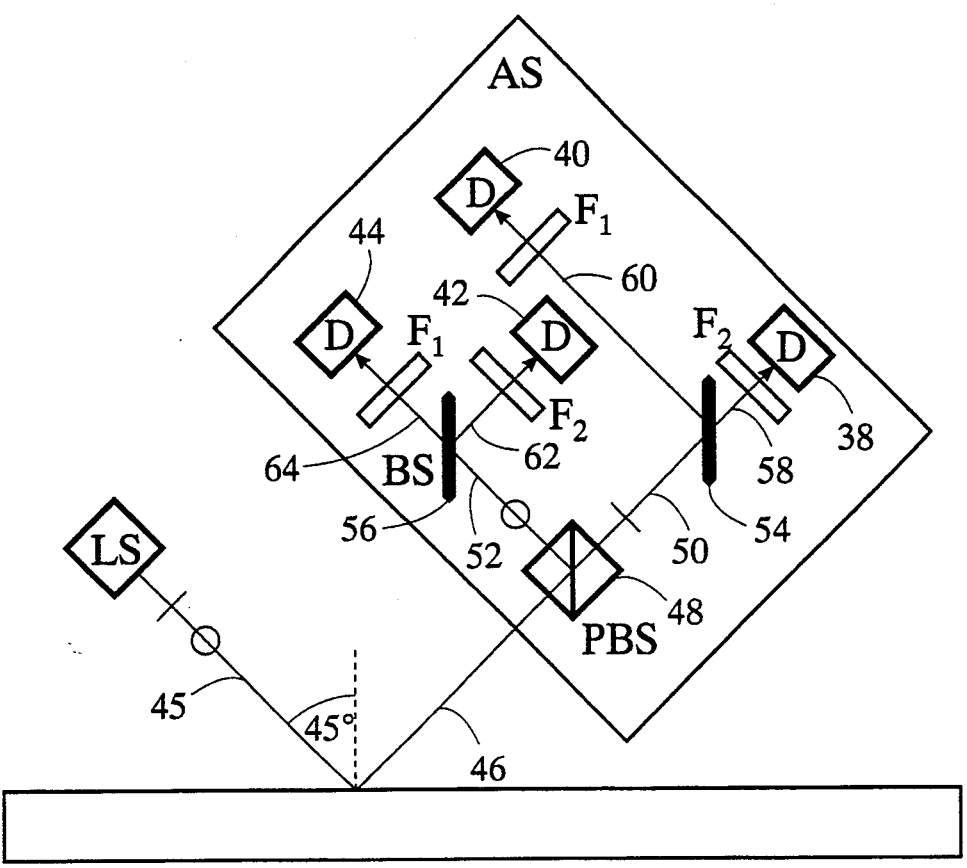
FIG. 5 is a schematic illustration of yet another embodiment of the device.

As seen in FIG. 5, the angle of incidence can be non-normal. This arrangement can be used in order to obtain additional information concerning molecular orientation in a direction perpendicular to the surface of the sheet. In FIG. 5, the angle of incidence is approximately 45°. The incident beam 45 is non-polarized. The reflected beam 46 is directed through a polarizing beam splitter (PBS) 48 which emits two orthogonally polarized beams 50, 52. Each of these in turn passes through a beam splitter (BS) 54, 56 respectively and becomes split each into two separate sub-beams 58, 60, 62, 64 respectively in order to enable the analysis of the same polarization at two different spectral bands, or wavelengths. To this end, filters $F_1$ and $F_2$, corresponding to wavelengths $\lambda_1$ and $\lambda_2$, respectively, are installed in the path of the subbeams 58, 60, 62, 64. The respective intensities of the filtered bands are detected by detectors (D) 38, 40, 42 and 44.

Figure 6:
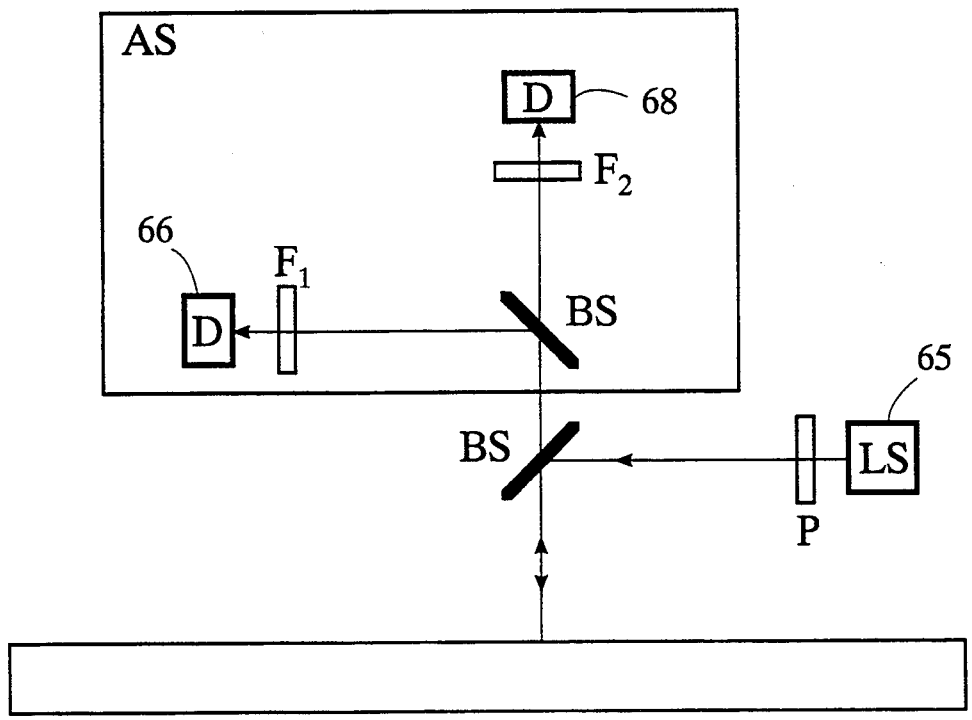
FIG. 6 is a schematic illustration of still another embodiment of the device.

Another embodiment of the device of the invention is illustrated in FIG. 6. The radiation beam from the light source 65 passes through a polarizer P which may be substituted by a polarizing beam splitter. Thus, the incident beam is polarized in one particular direction. The reflected beam passes through two beam splitters BS and is transmitted to the analyzing system AS which consists of two filters $F_1$ and $F_2$, centred at wavelengths $\lambda_1$ and $\lambda_2$, respectively. The respective intensities of the filtered spectral bands are detected by the detectors (D) 66, 68. In an actual example, the specific wavelengths were 1715 cm$^{-1}$ (5.83 μm) and 1253 cm$^{-1}$ (7.98 μm), see FIG. 7. The ratio of the reflectivities can be correlated with the degree of surface orientation in the direction of the polarization.

The version of FIG. 6 is particularly useful for characterizing biaxially oriented materials, if it is applied using two orthogonal polarizations as obtained by rotating the polarizer P, and compared to a non-oriented material as reference.

Information can also be obtained on other spectroscopically significant properties using the device of the invention (FIG. 5 and 6); for example, in the case of PET the band at 1341 cm$^{-1}$ (7.46 μm) is very sensitive to the degree of crystallinity. Other materials can be analyzed by developing reference patterns through routine experiments.

Figure 7:
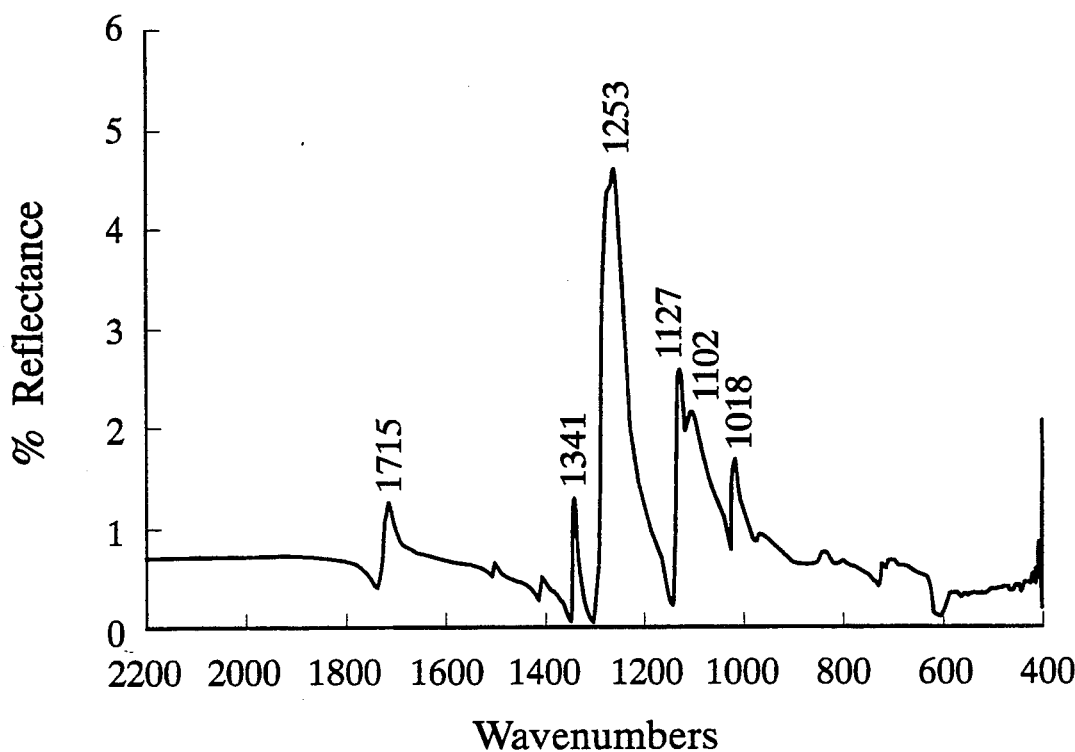
FIG. 7 is a graph of spectral reflectance of a polyethylene terephthalate (PET) film versus wavelength, at a polarization parallel to the draw direction of the film.
Figure 8:
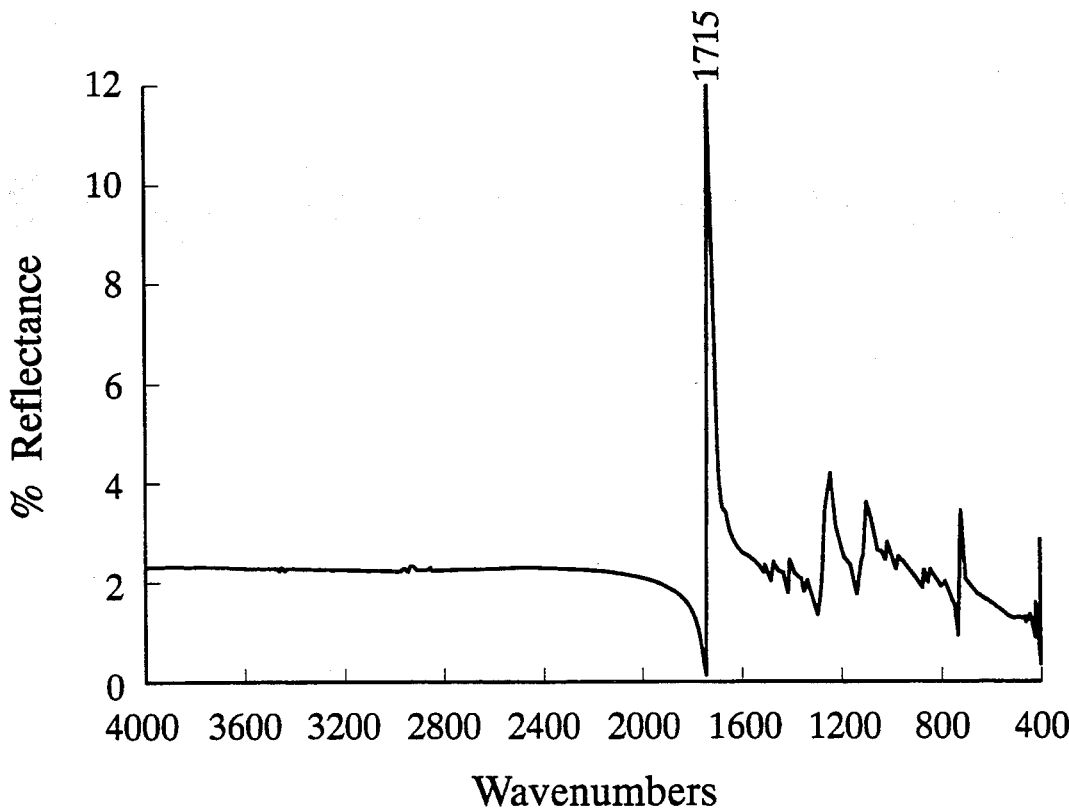
FIG. 8 is a graph of spectral reflectance of a PET film versus wavelength at a polarization perpendicular to the draw direction of the film.

Examples of spectral reflectance signals (specular reflectance at near-normal incidence) from an oriented PET sample are shown in FIGS. 7 and 8 for a polarization of the detected beam either parallel or perpendicular, respectively, to the draw direction of the film. It can be seen that by choosing, e.g. a filtered wavelength of 1715 cm$^{-1}$ (i.e. 5.83 μm), one obtains a specular reflectivity which changes by a factor of nearly 3 depending on whether the beam polarization is parallel or perpendicular to the oriented transition moments; the reflectivity would be identical for the two polarizations if the sample was perfectly isotropic.

Other wavelengths, or ratios involving different spectral peaks, can be chosen among those shown in FIGS. 7 and 8. One can also choose a wavelength outside of an absorbance band to obtain a reflectance which is related to the real part of the refractive index at orthogonal polarizations, i.e. to the material birefringence. In this case, however, substantial background reflectance may come from scattering from internal inhomogeneities (the beam penetration depth being relatively large outside of an absorption band). Consequently, operation at non-absorbing wavelengths is mainly limited to clear or perfectly smooth samples, where specular reflection can be separated from scattering by standard spatial filtering techniques.

Measurement times of the order of $10^{-5}$ seconds are possible, so that the speed of the running sheet could be as high as $10^2$ or $10^3$ m/sec.

It should be appreciated that the analysis of the surface molecular orientation and crystallinity does not have to have a highly quantitative character. Qualitative, comparative results are often satisfactory in view of the many variables in polymer processing. However, qualitative analysis using the device and the method of the invention is relatively straightforward even if, as in FIG. 6, there is only one polarized component of the reflected beam to analyze. In such a case, even the measurement of the reflectance at a single wavelength, compared with the reflectance of a calibration reference, would suffice to indicate qualitative differences in the material, but a ratio measurement is more reliable.

Details of the beam splitters, polarizing beam splitters, filters and detectors are not included within the present disclosure. These elements are all commonly known and used in optics.

We claim:

1. A method of determining a spectroscopically significant surface property, selected from surface molecular orientation or crystallinity, of a polymeric sheet, comprising:
   directing a substantially collimated optical radiation beam onto a surface of the sheet to produce a reflected optical radiation beam,
   extracting at least one plane-polarized component of the reflected optical radiation beam,
   detecting the intensity of the at least one component within at least one selected spectral band, and determining said spectroscopically significant surface property, selected from surface orientation or crystallinity, of said polymeric sheet by analyzing said intensity by comparison with a reference intensity.

2. The method according to claim 1, comprising:
   directing a substantially collimated optical radiation beam onto the surface of a polymeric sheet to produce a reflected optical radiation beam,
   splitting the beam into two components having different orthogonal polarization,
   detecting the intensity of each of the two components within at least one selected spectral band, and
   analyzing the intensity of each component by comparison with the intensity of the other component or a reference intensity.

3. The method of claim 1 wherein the optical radiation includes infrared radiation.

4. The method of claim 1 where the angle of incidence is approximately normal.

5. The method according to claim 1 wherein the intensity of spectral reflectance of the polarized component or components is detected and analyzed.

* * * * *